(12) United States Patent
Yuan et al.

(10) Patent No.: US 11,967,115 B1
(45) Date of Patent: Apr. 23, 2024

(54) COLOR MATCHING EVALUATION METHOD COMBINING SIMILARITY MEASURE AND VISUAL PERCEPTION

(71) Applicant: WUHAN TEXTILE UNIVERSITY, Wuhan (CN)

(72) Inventors: Li Yuan, Wuhan (CN); Jiaqi Xiong, Wuhan (CN); Jiachen Shen, Wuhan (CN); Shengjie Yang, Wuhan (CN); Xinru Wu, Wuhan (CN)

(73) Assignee: WUHAN TEXTILE UNIVERSITY, Wuhan (CN)

( * ) Notice: Subject to any disclaimer, the term of this patent is extended or adjusted under 35 U.S.C. 154(b) by 0 days.

(21) Appl. No.: 18/398,277

(22) Filed: Dec. 28, 2023

(30) Foreign Application Priority Data

Jan. 5, 2023 (CN) .......................... 202310016898.0

(51) Int. Cl.
  *G06T 7/90* (2017.01)
  *A61B 3/113* (2006.01)
  *G06T 11/00* (2006.01)

(52) U.S. Cl.
  CPC .............. *G06T 7/90* (2017.01); *A61B 3/113* (2013.01); *G06T 11/001* (2013.01); *G06T 2207/10024* (2013.01)

(58) Field of Classification Search
  CPC .................. G06T 7/90; G06T 11/001; G06T 2207/10024; A61B 3/113
  See application file for complete search history.

(56) References Cited

U.S. PATENT DOCUMENTS 11,107,257 B1 * 8/2021 Diverdi ............ G06F 18/23213
2009/0135267 A1   5/2009 Ishiga
(Continued)

FOREIGN PATENT DOCUMENTS

CN   109389591 A   2/2019
CN   110638471 A   1/2020

OTHER PUBLICATIONS

Luyan Zhang, et al., Characteristics of Extracted Main Colors and Application thereof in Patterns, Arts and Design (Theories), pp. 37-38, issued dated Jun. 30, 2019.
(Continued)

*Primary Examiner* — Yu Chen
(74) *Attorney, Agent, or Firm* — Daniel M. Cohn; Howard M. Cohn

(57) ABSTRACT

The present disclosure discloses a color matching evaluation method combining similarity measure and visual perception. The method includes: firstly, constructing an image database with rich color information; extracting main colors from an acquired image using an improved clustering method for color matching; generating a corresponding palette using an intelligent color matching recommendation system, and evaluating a palette similarity using a minimum color difference model; then, recoloring the corresponding image using the generated palette through an image recoloring technology to obtain a recolored image, and calculating a structural similarity between the source image and the recolored image; performing feature level adaptive weighted fusion on the palette similarity and the structural similarity, and performing an eye movement tracking experiment on the source image and the recolored image to obtain visual perception data of the images.

8 Claims, 3 Drawing Sheets

(56) References Cited

U.S. PATENT DOCUMENTS

| | | | |
|---|---|---|---|
| 2018/0122053 A1* | 5/2018 | Cohen | G06T 7/90 |
| 2021/0042965 A1* | 2/2021 | Phogat | G06V 10/763 |

OTHER PUBLICATIONS

Leida Li et al., Color image quality assessment based on sparse representation and reconstruction residual, Journal of Visual Communication and Image Representation, vol. 38, pp. 550-560, issued dated Jul. 31, 2016.

* cited by examiner

COLOR MATCHING EVALUATION METHOD COMBINING SIMILARITY MEASURE AND VISUAL PERCEPTION

CROSS-REFERENCE TO RELATED APPLICATIONS

The application claims priority of Chinese patent application CN202310016898.0, filed on Jan. 5, 2023, which is incorporated herein by reference in its entireties.

TECHNICAL FIELD

The present disclosure belongs to the field of color management and science, and particularly, to a color matching evaluation method combining similarity measure and visual perception.

BACKGROUND

Color is a subjective feeling generated by the stimulation of an external light source on human visual senses. In addition to following the physical law, color is also subject to physiological and psychological constraints. Color matching always runs through the lifecycle of the design of a product. According to statistical results of the International Fashion Color Association, a reasonable color matching relationship can bring an additional value of 10% to 25% to the product. In the design process, due to the lack of scientific and effective color matching evaluation methods, designers can often use a subjective empirical method and a manual visual method only to judge the harmony, beauty, and similarity of a color matching. This subjective and complex judgment method significantly affects the efficiency of designing a product by a designer and the quality of the design. Especially in a specific application field of color design, relying on the subjective empirical evaluation method often cannot meet the design-production-sales mode of existing "fast fashion". Therefore, based on image processing and mode recognition, a color matching evaluation method combining similarity measurement and visual perception is proposed to solve the problem that the existing color matching evaluation method only focus on subjective perception and lacks an objective measurement method. This evaluation method can provide an effective guidance for the field of color management and practical production mitigation, and has an important theoretical research value and a broad application prospect.

At the present stage, image aesthetic measures at home and abroad can be roughly divided into reference-based image aesthetic measure and reference-free image aesthetic measure. For example, a similarity of image is evaluated by using a method such as structural similarity (SSIM) to indirectly evaluate the aesthetic perception of the images. These evaluation indicators measure a similarity between the images by calculating a statistical difference in corresponding pixel points between two images. However, although these methods measure images objectively, these methods do not take human visual perception into account. A perception mechanism of a human visual system (HVS) for images is based on a combination of a macro perception and detail perception of the images, and is not sensitive to differences and offsets of pixel points within a small range. Therefore, due to the neglect of the perception characteristic of human eyes, the above evaluation indicators often have such a drawback that similarity evaluation results do not match a subjective perception in practical applications.

In addition, the reference-free image aesthetic measure is mainly completed by techniques such as deep learning. A main idea of deep learning is to obtain a pre-trained model based on prior network model knowledge by pre-training existing image aesthetic evaluation datasets using network model of a convolutional neural network, and train existing samples using technical means such as transfer learning, thus achieving a technical purpose of image aesthetic evaluation. However, this deep learning method using the transfer learning and the pre-trained model often has a high requirement on the technical means, and has a complex computation process, which does not meet the current design requirements.

It should be pointed out that in some of the image generation tasks described above, in order to better represent aesthetic measures of generated images, some methods also compare source image contents with the generated images. Meanwhile, color matching schemes involve combinations of different colors. In a color matching scheme taking a palette (an image composed of a plurality of color blocks) as a carrier, and a position of each color also affects the aesthetic evaluation of the color matching scheme. During the evaluation of the color matching scheme jointly determined by many factors, how to establish a scientific subjective and objective evaluation system for color matching schemes and color matching schemes recommended and generated by a recommendation system is a key and difficult point in the field of color management and science.

SUMMARY

For the current situation and problems described above, the present disclosure provides a color matching evaluation method combining similarity measure and visual perception by taking a palette as an application carrier. This method performs similarity measure and aesthetic evaluation measure on color matching schemes in three dimensions: palette content, image content, and visual perception. A color matching evaluation indicator model is constructed, which can objectively, instantly, and effectively evaluate a similarity and aesthetic feeling between the color matching schemes, thereby significantly improving the color matching efficiency in design and production.

In order to solve the problems mentioned in the background section, the present disclosure provides a color matching evaluation method combining similarity measure and visual perception.

A technical solution of the present disclosure is a color matching evaluation method combining similarity measure and visual perception, specifically including the following steps:

Step 1, acquiring sample images, and constructing a to-be-tested sample image database;

Step 2, improving a K-Means algorithm by using a silhouette coefficient method, and extracting main colors of the sample images to obtain a subject color palette P1 corresponding to each image;

Step 3, generating corresponding palettes P2 using an intelligent color recommendation system according to the main colors of the samples; and Step 4, if each palette is a combination of n color blocks, generating auxiliary palettes using P1 and P2, calculating minimum color differences of the paired palettes through a color difference model, and converting the minimum color differences into similarity measures as an evaluation indicator I;

Step 5, performing color transfer on the source sample images using the generated palettes P2 to obtain corresponding paired images;

Step 6, calculating structural similarities between the paired images, and marking results as an evaluation indicator II;

Step 7, conducting an eye movement tracking experiment on the source sample images and sample images subjected to the color transfer to obtain eye movement data between the paired images, converting the eye movement data into a visual perception measure, and marking the visual perception measure as an evaluation indicator III;

Step 8, assigning different weights to the evaluation indicator I and the evaluation indicator II to construct an image-content-based evaluation system; and Step 9, calculating Pearson correlation coefficients for the image-content-based evaluation system corresponding to the different weights and the evaluation indicator III in Step 8, and obtaining an optimal evaluation indicator corresponding to an optimal weight.

It should be noted that in Step 1, the acquired sample images are classified from the perspective of attributes and styles and all have rich color information. Realistic photography landscape images and realistic illustrations come from images posted by authoritative institutions such as Chinese geography. Freehand art paintings and Chinese and Western oil painting are collected from works of art of Vincent van Gogh, Monet, Margaret, Qi Baishi, Wu Guanzhong, Zhang Daqian, et al. All the collected images are available.

It should be noted that in Step 2, since color features contained in the respective sample images are inconsistent, quantities of extracted main colors will be different. Therefore, a traditional K-Means method for extracting fixed main colors is not applicable to the present disclosure. Based on this, the present disclosure provides an adaptive K-Means method to extract subject colors of samples. Since a K value is a quantity of main colors in a scenario of extracting colors, only the best K-value needs to be determined in the algorithm. The improved adaptive method is to use the silhouette coefficient method to obtain the best K value in the algorithm according to the input images. The K-Means algorithm and the silhouette coefficient method involve Formulas I to II.

$$J = \sum_{n=1}^{N} \sum_{k=1}^{K} r_{nk} \|c_{(n)} - \mu_k\|^2 \quad \text{Formula I}$$

$$s = \begin{cases} 1 - \dfrac{a}{b}, & a < b \\ 0, & a = b \\ \dfrac{b}{a} - 1, & a > b \end{cases} \quad \text{Formula II}$$

Where J represents a sum of distances between all types; n represents an index of a pixel in a background image; C(n) represents a color value of the pixel; N represents a total number of sample color data; K represents a quantity of color types; k represents a kth type of color; $r_{nk}$ is two-component, indicating whether a current color belongs to the kth type of color; $\mu_k$ represents a clustering center of the $k^{th}$ type of color; a represents an average distance between a sample point and all other points in the same cluster, namely, a similarity between the sample point and other points in the same cluster; b represents an average distance between the sample point and all points in the next nearest cluster, namely, a similarity between the sample point and other points in the next nearest cluster; s represents a value of a silhouette coefficient, wherein if s is closer to 1, a clustering effect is better; and if s is closer to −1, a clustering effect is worse.

It should be noted that in Step 3, the intelligent color recommendation system refers to an intelligent color matching recommendation system taking a color harmony degree as a mechanism and taking learning from big sample data as a technical background. Common color matching recommendation systems include software tools such as ColorMind, ColorHunt, PaletteRepublic, and ColorPick. The intelligent color recommendation system can automatically generate other colors that match a color harmony degree of a fixed color according to an input palette and by fixing some colors in the palette. Most intelligent color recommendation systems are implemented by an image translation model in a generative adversarial network, and a target function of the image translation model is as shown in Formulas III to V.

$$L_{cGAN}(G, D) = E_{x,y}[\log D(x, y)] + E_{x,z}[\log(1 - D(x, G(x, z)))] \quad \text{Formula III}$$

$$L_{L1}(G) = E_{x,y,z}[\|y - G(x, z)\|_1] \quad \text{Formula IV}$$

$$G^* = \arg\min_G \max_D L_{cGAN}(G, D) + \lambda L_{L1}(G) \quad \text{Formula V}$$

Where $L_{cGAN}(G,D)$, $L_{L1}(G)$, E respectively represent loss of a network model, L1 normal form loss, and a mathematical expectation of a distribution function; x, y, z, G, D, λ respectively represent weights of a real image, a generated false image, random noise, a generator, a discriminator, and the L1 loss; and G* represents a target function of a generator of the image translation model applicable to the intelligent color recommendation system.

It should be noted that in Step 4, the minimum color difference model suitable for evaluating the palette similarity proposed by the present disclosure uses the paired palettes (the original palettes and the palettes after color recommendation) in Step 3. The method achieves calculation by introducing an intermediate palette. A specific implementation method is as follows:

Step1: marking an original palette as P1, marking a generated palette as P2, calculating color differences respectively from the n colors of P2 to the first color of P1, and taking the color corresponding to a minimum color difference as the first color of a new palette;

Step2: calculating color differences respectively from the n colors of P2 to the second, third, and nth colors of P1, determining the second, third, and nth colors of the new palette according to the method described above, that is, generating a new auxiliary palette again using the generated palette P2, and marking the new auxiliary palette as P3;

Step3: calculating an average color difference between the original palette P1 and the palette P3, wherein an average color difference calculation method includes: respectively calculating color differences between the corresponding colors of the two palettes (between the ith color of the palette P1 and the $i^{th}$ color of the palette P3), and a calculation formula is shown in Formula XI, where i, n, and Ci represent the $i^{th}$ pair of colors, a total number of the colors of the palettes, and the average color difference of the corresponding $i^{th}$ colors, and the minimum color difference from the palette P1 to the palette P2 is marked as $m_1$;

$$m_1 = \frac{\sum_{i=1}^{n} C_i}{n};$$ 
Formula VI

Step4: repeating the operation of Step2, generating a new auxiliary palette for P2 using the n colors of P1, and marking the new palette as P4;

Step5: calculating an average color difference between the generated palette P2 and the palette P4, and marking the minimum color difference from P2 to P1 as $m_2$; and Step6: performing calculation applicable to evaluating the palette similarity provided by the present disclosure, which is as shown in Formula VII:

$$m=(m_1+m_2)/2$$ 
Formula VII where the color difference formulas respectively use CIELab, CIE94, and CIE2000, formulas of which are respectively as shown in Formula VIII to Formula X, $$CIE_{lab} = \sqrt{(L_2-L_1)^2+(a_2-a_1)^2+(b_2-b_1)^2};$$ 
Formula VIII $$CIE94 = \sqrt{\left(\frac{\Delta L}{K_L S_L}\right)^2+\left(\frac{\Delta C_{ab}}{K_c S_c}\right)^2+\left(\frac{\Delta H_{ab}}{K_H S_H}\right)^2};$$ 
Formula IX $$CIEDE2000 = \sqrt{\left(\frac{\Delta L}{K_L S_L}\right)^2+\left(\frac{\Delta C_{ab}}{K_c S_c}\right)^2+\left(\frac{\Delta H_{ab}}{K_H S_H}\right)^2+R_r\left(\frac{\Delta C}{K_c S_c}\right)\left(\frac{\Delta H_{ab}}{K_H S_H}\right)};$$ 
Formula X where $L_1$, $L_2$, $a_1$, $a_2$, $b_1$, and $b_2$ respectively represent Lab components of two colors during calculation of a color difference; $\Delta L'$, $\Delta C'_{ab}$, and $\Delta H'_{ab}$ respectively represent a brightness difference, a saturation difference, and a hue difference between two colors; $K_L$, Kc, and $\mu_y$ σβαγ are three constant parameters; and $S_L$, $S_c$, $S_H$, and $R_T$ are intermediate variables obtained through calculation of $\Delta L'$, $\Delta C'_{ab}$, and $\Delta H'_{ab}$.

It should be noted that in Step 4, Formula VII is normalized, and a normalized maximum theoretical value is subtracted by a normalized result. The reason is that in Step 4, a color difference between the paired palettes is calculated, but a main purpose of the model constructed in the present disclosure is to obtain a similarity between the paired palettes. Therefore, the maximum theoretical value is used to be subtracted by the difference to obtain the similarity measure between the palettes. A normalization method and the similarity measure are as shown in Formulas XI to XII, $$M = \frac{m-m\_min}{m\_max-m\_min};$$ 
Formula XI $$S = 1-M;$$ 
Formula XII wherein m, m_min, m_max respectively represents the minimum color difference between the palette P1 and the palette P2 and the minimum color difference and maximum color difference of all the palettes, and M and S represent the normalized result and the similarity measure between the palettes;

It should be noted that in Step 5, the present disclosure proposes evaluating color matching schemes in conjunction with image contents. That is, the generated color palette is used to perform the color transfer on the source images using a paper Palettenet method, and a professional artist is invited to evaluate image effects after color transfer, so as to remove recolored images with poor image effects.

It should be noted that in Step 6, the structural similarity SSIM between the recolored samples screened by the professional artist in Step 5 and their corresponding source images is calculated. A structural similarity is an indicator for measuring a similarity between two images, which is commonly used for evaluating an image similarity and image quality. Formulas are as shown in Formula XIII to Formula XVI.

$$l(x,y) = \frac{2\mu_x\mu_y+c_1}{\mu_x^2+\mu_y^2+c_1};$$ 
Formula XIII $$c(x,y) = \frac{2\sigma_x\sigma_y+c_2}{\sigma_x^2+\sigma_y^2+c_2};$$ 
Formula XIV $$s(x,y) = \frac{\sigma_{xy}+c_3}{\sigma_x\sigma_y+c_3};$$ 
Formula XV $$SSIM = l(x,y)^\alpha \times c(x,y)^\beta \times s(x,y))^\gamma;$$ 
Formula XVI where x and y respectively represent two images needing to be compared; $l(x, y)$, $c(x, y)$, and $s(x, y)$ represent brightness comparison, contrast comparison, and structure comparison; $\mu_x$, $\mu y$, $\sigma_x$, $\sigma_y$, and $\sigma_{xy}$ respectively represent a mean value of x, a mean value of y, a standard deviation of x, a standard deviation of y, and a covariance between x and y; $c_1$, $c_2$, and $c_3$ are constants, respectively, to avoid an error where the denominator is 0, $c3=c_2/2$; and in actual calculation, $\alpha$, $\beta$, and $\gamma$ are all set to be 1.

It should be noted that in Step 7, a TobiiX2-30 eye tracker is used to acquire the visual perception data. Images under test in the eye movement tracking experiment are composed of the original data samples and the recolored samples, respectively. 50 art school students are invited to participate in the eye movement tracking experiment. Each group of experimental samples combination had an experimental duration of 20 seconds. After the experiment on all the images under test has been completed, eye movement tracking data is recorded, and an average eye movement indicator of each image is recorded. Due to the fact that average fixation time, an average quantity of fixation points, and a first fixation duration can better reflect the visual perception, average eye movement data is obtained by weighting the three types of data according to fixed weights after the three types of data are normalized.

It should be noted that in Step 8, in the present disclosure, the evaluation indicator I and the evaluation indicator II which are formed by weighting different weights, so as to obtain the image-content-based evaluation system. A feature level fusion policy fuses the similarity measure between the palettes with the structural similarity measure, and converts the measures into a percentage form to obtain an overall similarity. The fusion manner is as shown in Formula XVII:

$$SIM=\omega*S+(1-\omega)*SSIM$$ 
Formula XVII where ω is a variable weight; S is the similarity measure between the palettes, and SSIM is the structural similarity between the images.

In Step 9, the Pearson correlation coefficient is calculated for the image-content-based evaluation system and the evaluation indicator III. The Pearson correlation coefficient is used for measuring a correlation degree between two variables, with a value between −1 and 1. A calculation formula of the Pearson correlation coefficient is as shown in Formula XVIII, where X and Y are independent variables; cov(XY) represents a covariance between the variable X and the variable Y; and σ is a standard deviation.

$$\rho = \frac{cov(XY)}{\sigma_x \sigma_y} \qquad \text{Formula XVIII}$$

Correlations of the indicator I and the indicator II weighted under different weights to the indicator III are calculated, and an optimal evaluation indicator system corresponding to the optimal weight is obtained on the basis of this.

The present disclosure takes color matching schemes as specific application objects. Firstly, a to-be-tested sample image database is constructed, and adaptive main color extraction is performed on sample images; some colors are locked for the extracted color matching schemes for color recommendation to obtain new color matching schemes. afterwards, a minimum palette color difference model is constructed for paired color matching schemes by introducing auxiliary palettes; afterwards, a color transfer technology is used to recolor recommended palettes onto the source images to obtain recolored images corresponding to the constructed sample image database, and structural similarities between paired images are calculated; variable weight fusion is performed on similarities of palettes and the structural similarities of the images using different weights, and the weights have a range of [0, 1]; Image-content-based similarities under different weights are calculated; and finally, the aesthetics of the images is evaluated through visual perception; an eye movement tracking technology is used to conduct an experiment on the source images and the images after color transfer; and visual perception data is obtained. Pearson correlation coefficient analysis is performed on the visual perception data obtained through the experiment and a result obtained after the variable weight fusion performed using different weights, to obtain the optimal weight and the optimal evaluation indicator system corresponding to the optimal weight, thus achieving aesthetic measure of the color matching schemes from the perspective of similarity and visual perception. The present disclosure has an important guiding significance for production processes of color related industries. Due to the significant application prospect and value of the technical solutions of the present disclosure, protecting the technical solutions of the present disclosure will be of great significance for the color science field and the color management field to compete for the international leading position in China.

DETAILED DESCRIPTION OF THE EMBODIMENTS

Specific implementations of the technical solutions of the present disclosure can be carried out by a person skilled in the art using relevant data and a computer software technology. A specific description of an embodiment of the present disclosure is provided as follows in combination with the accompanying drawings.

Figure 1:
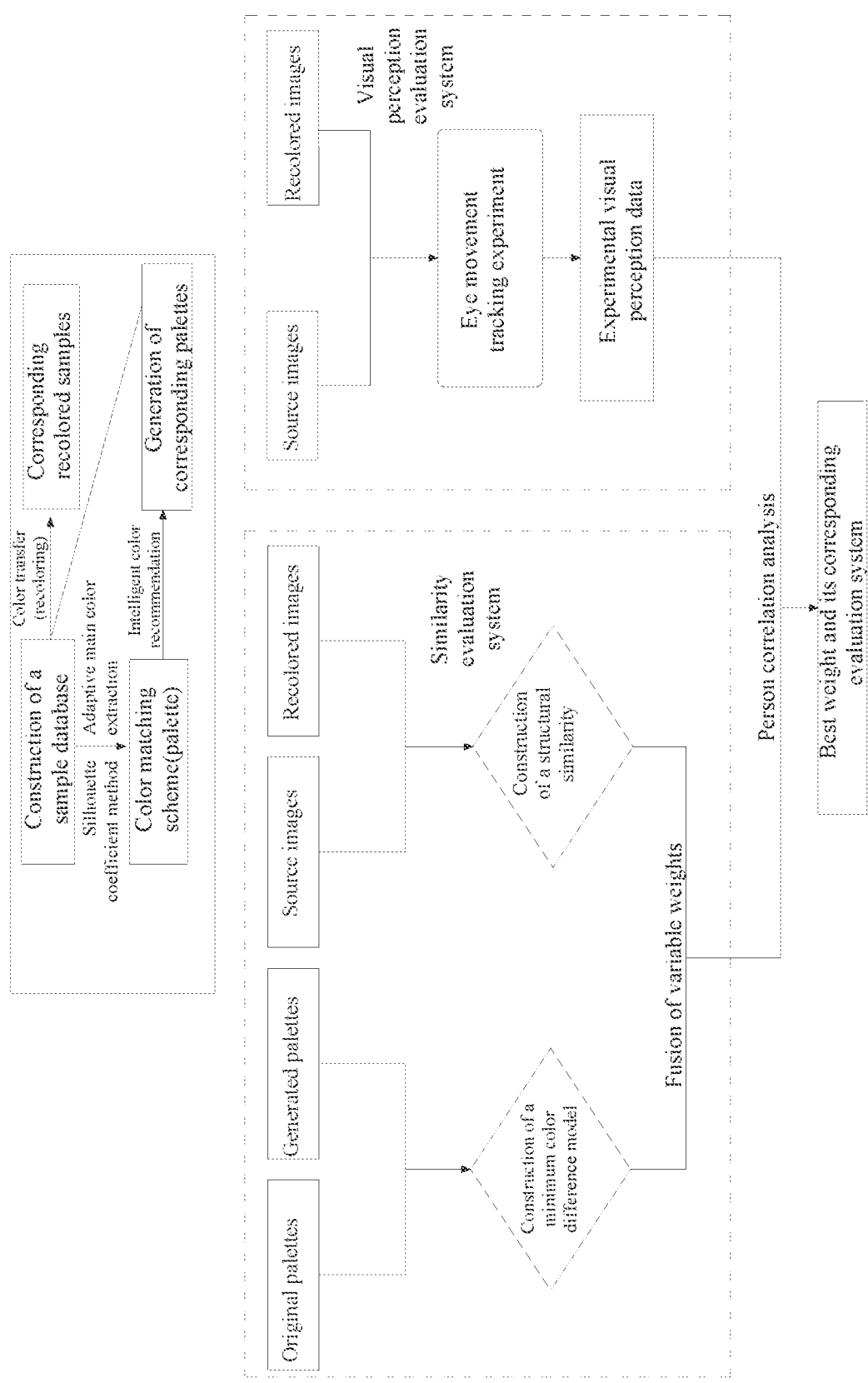
FIG. 1 is a flowchart of the present disclosure.
Figure 2:
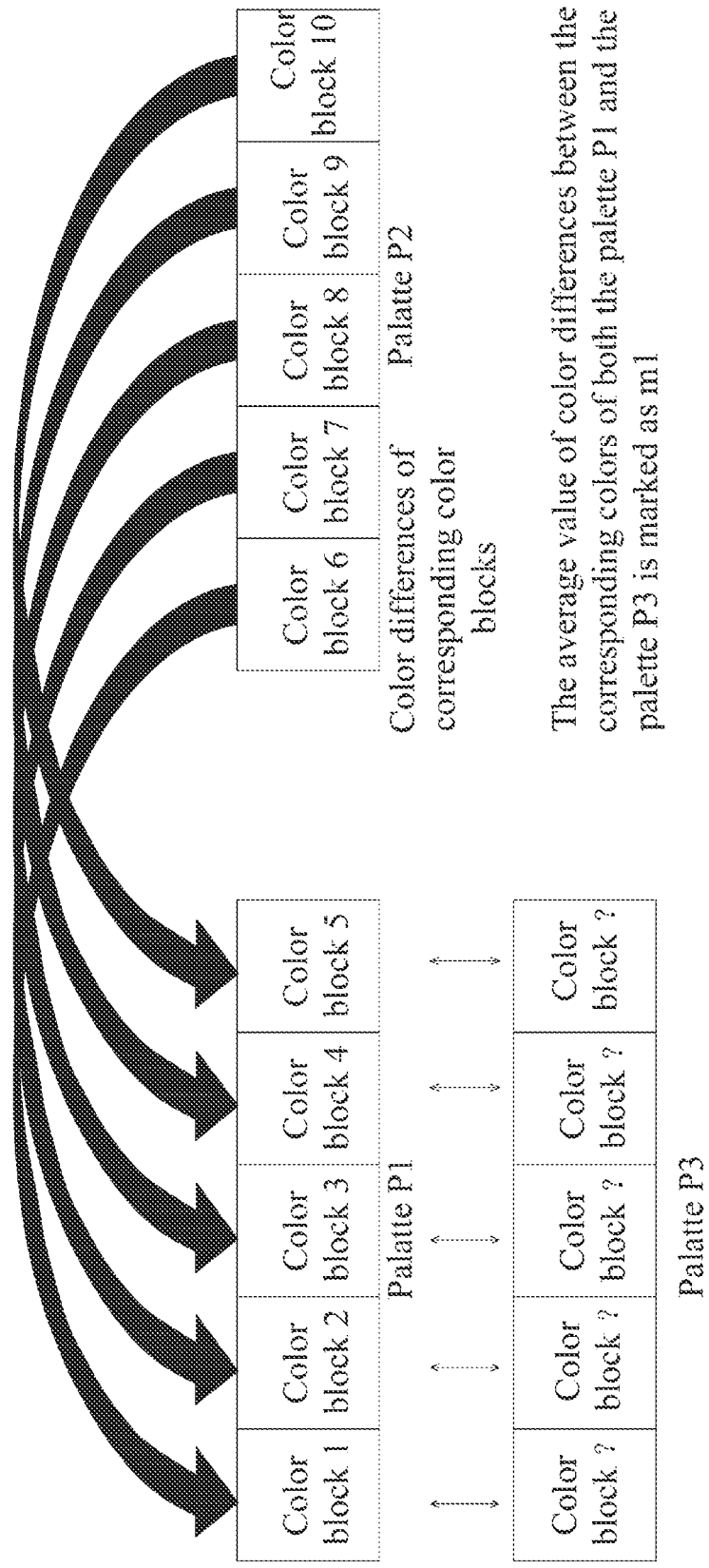
FIG. 2 is a calculation step of an auxiliary palette P3 and color difference calculation according to the present disclosure.
Figure 3:
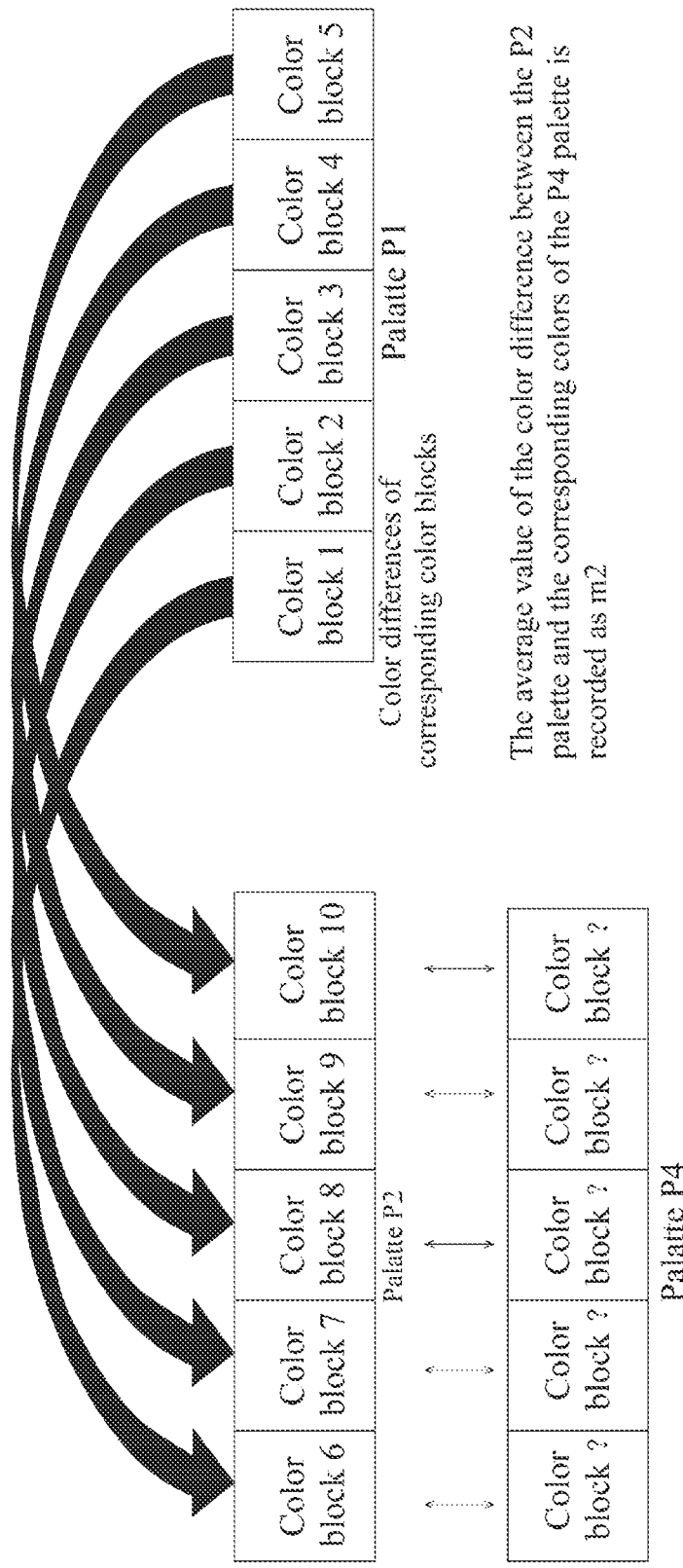
FIG. 3 is a calculation step of an auxiliary palette P4 and calculation of a minimum color difference between a palette P1 and a palette P2.

As shown in FIG. 1, the embodiment provides a color matching evaluation method combining visual perception and similarity measure. An objective quantitative analysis and evaluation model is constructed for aesthetic evaluation of color matching in color management, which can provide guidance for designers in the color management field to match colors. Algorithmic operation devices include ultra-micro 7048GR-TR, a Windows10 operating system, an Intel® Xeon® E5-2678V3*2CPU, a 128 G internal memory, and a NVIDIA TeslaM40*4 operation card. An algorithm development environment is MATLAB R2016a and Python 3.6. Hardware devices include a Tobii X2-30 eye tracker and Tobii Pro Lab series software. It should be noted that the present disclosure is not limited to the application supports of the samples and software and hardware platforms described above, but is also applicable to any corresponding data and software and hardware platform that can implement the method of the present disclosure.

The embodiment mainly includes the following steps:

1) Sample Images are Acquired, and a to-be-Tested Sample Image Database is Constructed As mentioned above, self-constructed sample datasets are used in this embodiment. In order to make experimental data and experimental conclusions of the present disclosure more scientific and robust, the present disclosure constructs sample sets according to styles and attributes of the sample images, and divides the sample sets into types such as realistic photography landscape images, realistic illustrations, freehand art paintings, and freehand Chinese and Western oil paintings. This embodiment involves a total of 800 samples in the above four types of sample sets.

2) A K-Means Algorithm is Improved by Using a Silhouette Coefficient Method, and Main Colors of the Sample Images are Extracted In this embodiment, color information contained in the respective samples is different, so that quantities of the main colors in the samples are different. Based on this, the present disclosure proposes using the improved K-Means algorithm to adaptively extract the main colors of the samples. The adaptive main control extraction method uses different K values to calculate a silhouette coefficient s. In a clustering process using different K values, this method determines an s that is closest to 1 to be the best K value with the best clustering effect, then uses the best K value to complete the clustering process, and calculates a K-Means target function J. The improved method is to apply the silhouette coefficient method, which is the evaluation method of the K-Means algorithm, to the algorithm. The best K value is determined through iteration in the algorithm, and the determined best K value is the quantity of the adaptively extracted main colors. The K-Means algorithm and the silhouette coefficient method are as shown in Formula I to Formula II.

$$J = \sum_{n=1}^{N}\sum_{k=1}^{K} r_{nk} \|C(n) - \mu k\|^2 \qquad \text{Formula I}$$

$$s = \begin{cases} 1 - \dfrac{a}{b}, & a < b \\ 0, & a = b \\ \dfrac{b}{a} - 1, & a > b \end{cases} \qquad \text{Formula II}$$

Where J represents a sum of distances between all types; n represents an index of a pixel in a background image; C(n) represents a color value of the pixel; N represents a total number of sample color data; K represents a quantity of color types; k represents a kth type of color; $r_{nk}$ is two-component, indicating whether a current color belongs to the $k^{th}$ type of color; $\mu_k$ represents a clustering center of the $k^{th}$ type of color; a represents an average distance between a sample point and all other points in the same cluster, namely, a similarity between the sample point and other points in the same cluster; b represents an average distance between the sample point and all points in the next nearest cluster, namely, a similarity between the sample point and other points in the next nearest cluster; s represents a value of a silhouette coefficient, wherein if s is closer to 1, a clustering effect is better; and ifs is closer to −1, a clustering effect is worse.

3) Corresponding Palettes are Generated Using an Intelligent Color Recommendation System According to the Main Colors of the Samples.

In this embodiment, the intelligent color recommendation system used herein is an intelligent color recommendation system based on an image translation model. For details, refer to tool ColorMind. The intelligent color recommendation system based on the image translation model learns a color matching rule through deep learning according to the existing color matching schemes, recommends several colors of the original color matching schemes according to the learned color matching rule, and obtains a new color matching combination. The intelligent color recommendation system can well meet design needs of designers and assist the designers in quickly matching colors. A target function of the image translation model used in the present disclosure is as shown in Formula III to Formula V;

$$L_{cGAN}(G, D) = E_{x,y}[\log D(x, y)] + E_{x,z}[\log(1 - D(x, G(x, z)))] \quad \text{Formula III}$$

$$L_{L1}(G) = E_{x,y,z}[\|y - G(x, z)\|_1] \quad \text{Formula IV}$$

$$G^* = \arg\min_G \max_D L_{cGAN}(G, D) + \lambda L_{L1}(G) \quad \text{Formula V}$$

Where $L_{cGAN}(G,D)$, $L_{L1}(G)$, E respectively represent loss of a network model, L1 normal form loss, and a mathematical expectation of a distribution function; x, y, z, G, D, λ respectively represent weights of a real image, a generated false image, random noise, a generator, a discriminator, and the L1 loss; and G* represents a target function of a generator of the image translation model applicable to the intelligent color recommendation system.

4) In this embodiment, minimum color differences between paired palettes are calculated, which is implemented by introducing auxiliary palettes. Specific steps are as follows:

Step1: An original palette is marked as P1, and a generated palette is marked as P2; color differences respectively from n colors of P2 to a first color of P1 are calculated, and the color corresponding to a minimum color difference is taken as a first color of a new palette.

Step2: Color differences respectively from n colors of P2 to second, third, and nth colors of P1 are calculated, and second, third, and nth colors of the new palette are determined according to the method described above, that is, a new auxiliary palette is generated again using the generated palette P2 and the new auxiliary palette is marked as P3.

Step3: An average color difference between the original palette P1 and the palette P3 is calculated, wherein an average color difference calculation method includes: respectively calculating color differences between the corresponding colors of the two palettes (between an $i^{th}$ color of the palette P1 and an $i^{th}$ color of the palette P3), and a calculation formula is as shown in Formula VI:

$$m_1 = \frac{\sum_{i=1}^{n} C_i}{n}; \quad \text{Formula VI}$$

where i, n, and Ci represent the it h pair of colors, a total number of the colors of the palettes, and the average color difference of the corresponding $i^{th}$ colors, and the minimum color difference from the palette P1 to the palette P2 is marked as $m_1$.

Step4: The operation of Step2 is repeated; a new auxiliary palette is generated for P2 using the n colors of P1; and the new palette is marked as P4.

Step5: An average color difference between the generated palette P2 and the palette P4 is calculated, and the minimum color difference from P2 to P1 is marked as $m_2$.

Step6: Calculation applicable to evaluating the palette similarity provided by the present disclosure is performed, which is as shown in Formula VII.

$$m=(m_1+m_2)/2 \quad \text{Formula VII}$$

In the present disclosure, main color difference calculation models such as CIELab, CIE94, and CIE2000 are respectively used, formulas of which are respectively as shown in Formula VIII to Formula X:

$$CIE_{lab} = \sqrt{(L_2 - L_1)^2 + (a_2 - a_1)^2 + (b_2 - b_1)^2}; \quad \text{Formula VIII}$$

$$CIE94 = \sqrt{\left(\frac{\Delta L}{K_L S_L}\right)^2 + \left(\frac{\Delta C_{ab}}{K_c S_c}\right)^2 + \left(\frac{\Delta H_{ab}}{K_H S_H}\right)^2}; \quad \text{Formula IX}$$

$$CIEDE2000 = \sqrt{\left(\frac{\Delta L}{K_L S_L}\right)^2 + \left(\frac{\Delta C_{ab}}{K_c S_c}\right)^2 + \left(\frac{\Delta H_{ab}}{K_H S_H}\right)^2 + R_t\left(\frac{\Delta C}{K_c S_c}\right)\left(\frac{\Delta H_{ab}}{K_H S_H}\right)}; \quad \text{Formula X}$$

where $L_1$, $L_2$, $a_1$, $a_2$, $b_1$, and $b_2$ respectively represent Lab components of two colors during calculation of a color difference; ΔL', ΔC'ab', and ΔH'ab' respectively represent a brightness difference, a saturation difference, and a hue difference between two colors; $K_L$, $K_c$, and $K_H$ are three constant parameters; and $S_L$, $S_C$, $S_H$ and $R_T$ are intermediate variables obtained through calculation of ΔL', C'ab', and ΔH'ab'.

In this embodiment, the color difference values calculated above are normalized, and a normalization formula is as shown in Formula XI. The main purpose of constructing the color difference model in the present disclosure is to calculate a similarity between palettes, so that a normalized maximum theoretical value is used to be subtracted from a color-difference-normalized result to obtain a similarity measure between the palettes, which is as shown in Formula XII:

$$M = \frac{m - m\_min}{m\_max - m\_min}; \quad \text{Formula XI}$$

$$S = 1 - M; \quad \text{Formula XII}$$

wherein m, m_min, and m_max respectively represents the minimum color difference between the palette P1 and the palette P2 and the minimum color difference and maximum color difference of all the palettes, and M and S represent the normalized result and the similarity measure between the palettes.

5) Color Transfer is Performed on the Source Samples Using the Generated Palettes to Obtain Corresponding Paired Images In this embodiment, to determine the quality of a generated color matching scheme according to an image content, the present disclosure uses the generated palettes to perform the color transfer on the source images. In the present disclosure performs the color transfer on the source images using a Palette method, and a professional artist is invited to screen image effects after color transfer, so as to remove recolored images with poor image effects.

6) Structural Similarities Between the Paired Images are Calculated

In this embodiment, the structural similarities between the paired image samples are calculated, and the paired images are composed of the source samples and the corresponding recolored samples. A structural similarity is an indicator for measuring a similarity between two images, which is commonly used for evaluating an image similarity and image quality on the basis of image contents. Formulas are as shown in Formula XIII to Formula XVI.

$$l(x, y) = \frac{2\mu_x\mu_y + c_1}{\mu_x^2 + \mu_y^2 + c_1};$$  Formula XIII $$c(x, y) = \frac{2\sigma_x\sigma_y + c_2}{\sigma_x^2 + \sigma_y^2 + c_2};$$  Formula XIV $$s(x, y) = \frac{\sigma_{xy} + c_3}{\sigma_x\sigma_y + c_3};$$  Formula XV $$SSIM = l(x, y)^\alpha \times c(x, y)^\beta \times s(x, y)^\gamma;$$  Formula XVI where x and y respectively represent two images needing to be compared; $l(x, y)$, $c(x, y)$, and $s(x, y)$ represent brightness comparison, contrast comparison, and structure comparison; $\mu_x$, $\mu_y$, $\sigma_x$, $\sigma_y$, and $\sigma_{xy}$ respectively represent a mean value of x, a mean value of y, a standard deviation of x, a standard deviation of y, and a covariance between x and y; $c_1$, $c_2$, and $c_3$ are constants, respectively, to avoid an error where the denominator is 0, $c_3=c_2/2$; and in actual calculation, $\alpha$, $\beta$, and $\gamma$ are all set to be 1.

7) An eye movement tracking experiment is conducted on the source samples and the samples subjected to the color transfer to obtain eye movement data between the paired images, and the eye movement data is converted into a visual perception measure In this embodiment, a TobiiX2-30 eye tracker is used to acquire the visual perception data. Images under test in the eye movement tracking experiment are composed of the original data samples and the recolored samples, respectively. 50 art school students are invited to participate in the eye movement tracking experiment. Each group of experimental samples combination had an experimental duration of 20 seconds. After the experiment on all the images under test has been completed, eye movement tracking data is recorded, and an average eye movement indicator of each image is recorded. Due to the fact that average fixation time, an average quantity of fixation points, and a first fixation duration can better reflect the visual perception, the visual perception data is obtained by weighting the three types of data according to fixed weights after the three types of data are normalized.

8) A Feature Level Fusion Policy is Used to Fuse the Similarity Measure Between the Palettes with the Structural Similarity Measure to Obtain a Similarity Based on Palettes and Image Contents In this embodiment, a result of the similarity measure between the palettes and a result of the structural similarity measure are ideally independent. In the present disclosure, the feature level fusion policy is used to fuse the similarity measure between the palettes with the structural similarity measure, and convert the measures into a percentage form to obtain an overall similarity.

The fusion manner is as shown in Formula XVII:

$$SIM = \omega * S + (1-\omega) * SSIM$$  Formula XVII where $\omega$ is a variable weight; S is the similarity measure between the palettes, and SSIM is the structural similarity between the images.

9) Pearson correlation coefficient analysis is performed using the similarity based on image contents and the visual perception measure, and the weights in 8) are optimized to obtain the best weight, thus ultimately obtaining an evaluation indicator corresponding to the best weight.

In this embodiment, weight values of the results of the two similarity measures are optimized. A specific method is to calculate different weights of the results of the two similarity measures to obtain the overall similarity results under the different weights. The visual perception data in 7) is used to calculate Pearson correlation coefficients for the overall similarities under the different weights. Formulas for the Pearson correlation coefficient is as shown in Formula XVIII:

$$\rho = \frac{\mathrm{cov}(XY)}{\sigma_x\sigma_y}$$  Formula XVIII where X and Y are independent variables; $\mathrm{cov}(XY)$ represents a covariance between the variable X and the variable Y; and $\sigma$ is a standard deviation.

To verify the scientificity and robustness of the present disclosure, three color difference formulas, namely, CIELab, CIE94, and CIEDE2000, are used in the present disclosure to calculate the similarity. Three parameter optimization results corresponding to the three color difference formulas are shown in Table 1 to Table 3. The results show that the weight value $\omega$ is 0.6, the correlation coefficients of CIELab and CIEDE2000 reach 0.804 and 0.861 respectively, which are superior to results of experimental groups under other weights. The correlation coefficient of CIE94 reaches 0.760, which is second only to a case where the weights are all 0.5. Therefore, the present disclosure sets a weight ratio ($\omega$: $1-\omega$) between the result of the similarity measure between the palettes and the result of the structural similarity measure to 0.6:0.4, and the similarity measure and visual perception measure between combining palette contents and image contents under this weight can achieve the best effect of the evaluation model.

TABLE 1

Analysis (CIELab) of correlation between the similarity based on image contents and the visual perception measure

| Weight ω(1 − ω) | Person correlation coefficient |
|---|---|
| 0.0:1.0 | 0.515 |
| 0.1:0.9 | 0.596 |
| 0.2:0.8 | 0.639 |
| 0.3:0.7 | 0.678 |
| 0.4:0.6 | 0.721 |
| 0.5:0.5 | 0.786 |
| 0.6:0.4 | 0.804 |
| 0.7:0.3 | 0.747 |
| 0.8:0.2 | 0.692 |
| 0.9:0.1 | 0.642 |
| 1.0:0.0 | 0.583 |

TABLE 2

Analysis (CIE94) of correlation between the similarity based on image contents and the visual perception measure

| Weight ω(1 − ω) | Person correlation coefficient |
|---|---|
| 0.0:1.0 | 0.509 |
| 0.1:0.9 | 0.544 |
| 0.2:0.8 | 0.645 |
| 0.3:0.7 | 0.729 |
| 0.4:0.6 | 0.732 |
| 0.5:0.5 | 0.769 |
| 0.6:0.4 | 0.760 |
| 0.7:0.3 | 0.721 |
| 0.8:0.2 | 0.675 |
| 0.9:0.1 | 0.632 |
| 1.0:0.0 | 0.581 |

TABLE 3

Analysis (CIEDE2000) of correlation between the similarity based on image contents and the visual perception measure

| Weight ω(1 − ω) | Person correlation coefficient |
|---|---|
| 0.0:1.0 | 0.561 |
| 0.1:0.9 | 0.594 |
| 0.2:0.8 | 0.702 |
| 0.3:0.7 | 0.754 |
| 0.4:0.6 | 0.783 |
| 0.5:0.5 | 0.839 |
| 0.6:0.4 | 0.861 |
| 0.7:0.3 | 0.806 |
| 0.8:0.2 | 0.717 |
| 0.9:0.1 | 0.680 |
| 1.0:0.0 | 0.625 |

The specific embodiments described herein are only illustrative examples of the spirit of the present disclosure. A person skilled in the art to which the present disclosure belongs can make various modifications or supplements to the specific embodiments described or use similar manners to replace the specific embodiments, without deviating from the spirit of the present disclosure or going beyond the scope defined in the attached claims.

What is claimed is:

1. A color matching evaluation method combining similarity measure and visual perception, wherein the method comprises the following steps:

Step 1, acquiring sample images, and constructing a to-be-tested sample image database;

Step 2, improving a K-Means algorithm by using a silhouette coefficient method, and extracting main colors of the sample images to obtain a subject color palette P1 corresponding to each image;

Step 3, generating corresponding palettes P2 using an intelligent color recommendation system according to the main colors of the samples; and Step 4, if each palette is a combination of n color blocks, generating auxiliary palettes using P1 and P2, calculating minimum color differences of the paired palettes through a color difference model, and converting the minimum color differences into similarity measures as an evaluation indicator I;

an implementation of generating an auxiliary palette in Step 4 is as follows:

Step 1, marking an original palette as P1, marking a generated palette as P2, calculating color differences respectively from the n colors of P2 to the first color of P1, and taking the color corresponding to a minimum color difference as the first color of a new palette;

Step2, calculating color differences respectively from the n colors of P2 to the second, third, and nth colors of P1, determining the second, third, and nth colors of the new palette according to the method described above, that is, generating a new auxiliary palette again using the generated palette P2, and marking the new auxiliary palette as P3;

Step3, calculating an average color difference between the original palette P1 and the palette P3, wherein an average color difference calculation method comprises: respectively calculating color differences between the corresponding colors of the two palettes, that is, between the $i^{th}$ color of the palette P1 and the $i^{th}$ color of the palette P3, and a calculation formula is shown in Formula XI, wherein i, n, and Ci represent the $i^{th}$ pair of colors, a total number of the colors of the palettes, and the average color difference of the corresponding $i^{th}$ colors, and the minimum color difference from the palette P1 to the palette P2 is marked as $m_1$;

$$m_1 = \frac{\sum_{i=1}^{n} C_i}{n};$$ Formula VI

Step4, repeating the operation of Step2, generating a new auxiliary palette for P2 using the n colors of P1, and marking the new palette as P4; and Step5, calculating an average color difference between the generated palette P2 and the palette P4, and marking the minimum color difference from P2 to P1 as $m_2$;

a specific implementation of converting the minimum color differences into similarity measures as an evaluation indicator I in Step 4 is as follows:

firstly, calculating the minimum color difference between the palette P1 and the palette P2;

$m=(m_1+m_2)/2$ Formula VII; and then, subtracting a normalized maximum theoretical value from a color-difference-normalized result to obtain a similarity measure between the palettes, as shown in Formula XII, $$M = \frac{m - m\_min}{m\_max - m\_min};$$ Formula XI $S = 1 - M;$ Formula XII wherein m, m_min, and m_max respectively represents the minimum color difference between the palette P1 and the palette P2 and the minimum color difference and maximum color difference of all the palettes, and M and S represent the normalized result and the similarity measure between the palettes;

Step 5, performing color transfer on the source sample images using the generated palettes P2 to obtain corresponding paired images;

Step 6, calculating structural similarities between the paired images, and marking results as an evaluation indicator II;

Step 7, conducting an eye movement tracking experiment on the source sample images and sample images subjected to the color transfer to obtain eye movement data between the paired images, converting the eye movement data into a visual perception measure, and marking the visual perception measure as an evaluation indicator III;

Step 8, assigning different weights to the evaluation indicator I and the evaluation indicator II to construct an image-content-based evaluation system; and Step 9, calculating Pearson correlation coefficients for the image-content-based evaluation system corresponding to the different weights and the evaluation indicator III in Step 7, and obtaining an optimal evaluation indicator corresponding to an optimal weight.

2. The color matching evaluation method combining the similarity measure and the visual perception according to claim 1, wherein a specific implementation of Step 2 is as follows:

$$J = \sum_{n=1}^{N}\sum_{k=1}^{K} r_{nk}\|C(n) - \mu_k\|^2; \quad \text{Formula I}$$

$$s = \begin{cases} 1 - \frac{a}{b}, & a < b \\ 0, & a = b \\ \frac{b}{a} - 1, & a > b \end{cases} \quad \text{Formula II}$$

wherein J represents a sum of distances between all types; n represents an index of a pixel in a background image; C(n) represents a color value of the pixel; N represents a total number of sample color data; K represents a quantity of color types; k represents a $k^{th}$ type of color; $r_{nk}$ is two-component, indicating whether a current color belongs to the $k^{th}$ type of color; $\mu_k$ represents a clustering center of the $k^{th}$ type of color; a represents an average distance between a sample point and all other points in the same cluster, namely, a similarity between the sample point and other points in the same cluster; b represents an average distance between the sample point and all points in the next nearest cluster, namely, a similarity between the sample point and other points in the next nearest cluster; s represents a value of a silhouette coefficient, wherein if s is closer to 1, a clustering effect is better; ifs is closer to −1, a clustering effect is worse; the main color extraction method described above is to calculate the silhouette coefficient s using different K values; in a clustering process using different K values, determine an s that is closest to 1 to be a K value representing the best clustering effect; and complete the clustering process using the best K value, and calculate a K-Means objective function J.

3. The color matching evaluation method combining the similarity measure and the visual perception according to claim 1, wherein in Step 3 of generating corresponding palettes using an intelligent color recommendation system based on an image translation model, a target function of the image translation model is as shown in Formulas III to V, $$L_{cGAN}(G, D) = E_{x,y}[\log D(x, y)] + E_{x,z}[\log(1 - D(x, G(x, z)))]; \quad \text{Formula III}$$

$$L_{L1}(G) = E_{x,y,z}[\|y - G(x, z)\|_1]; \quad \text{Formula IV}$$

$$G^* = \arg\min_G\max_D L_{cGAN}(G, D) + \lambda L_{L1}(G); \quad \text{Formula V}$$

wherein $L_{cGAN}(G,D)$, $L_{L1}(G)$, E respectively represent loss of a network model, L1 normal form loss, and a mathematical expectation of a distribution function; x, y, z, G, D, λ respectively represent weights of a real image, a generated false image, random noise, a generator, a discriminator, and the L1 loss; and G* represents a target function of a generator of the image translation model applicable to the intelligent color recommendation system.

4. The color matching evaluation method combining the similarity measure and the visual perception according to claim 1, wherein the color difference model used in Step 4 comprises color difference calculation models CIELab, CIE94, and CIE2000, formulas of which are respectively as shown in Formulas VIII to X, $$CIE_{lab} = \sqrt{(L_2 - L_1)^2 + (a_2 - a_1)^2 + (b_2 - b_1)^2}; \quad \text{Formula VIII}$$

$$CIE94 = \sqrt{\left(\frac{\Delta L}{K_L S_L}\right)^2 + \left(\frac{\Delta C_{ab}}{K_c S_c}\right)^2 + \left(\frac{\Delta H_{ab}}{K_H S_H}\right)^2}; \quad \text{Formula IX}$$

$$CIEDE2000 = \sqrt{\left(\frac{\Delta L}{K_L S_L}\right)^2 + \left(\frac{\Delta C_{ab}}{K_c S_c}\right)^2 + \left(\frac{\Delta H_{ab}}{K_H S_H}\right)^2 + R_t\left(\frac{\Delta C}{K_c S_c}\right)\left(\frac{\Delta H_{ab}}{K_H S_H}\right)}; \quad \text{Formula X}$$

wherein $L_1$, $L_2$, $a_1$, $a_2$, $b_1$, and $b_2$ respectively represent Lab components of two colors during calculation of a color difference; $\Delta L'$, $\Delta C'_{ab}$, and $\Delta H'_{ab}$ respectively represent a brightness difference, a saturation difference, and a hue difference between two colors; $K_L$, $K_C$, and $K_H$ are three constant parameters; and $S_L$, $S_c$, $S_H$, and $R_T$ are intermediate variables obtained through calculation of $\Delta L'$, $\Delta C'_{ab}$, and $\Delta H'_{ab}$.

5. The color matching evaluation method combining the similarity measure and the visual perception according to claim 1, wherein calculation formulas of the structural similarity in Step 6 are as follows:

$$l(x, y) = \frac{2\mu_x\mu_y + c_1}{\mu_x^2 + \mu_y^2 + c_1}; \quad \text{Formula XIII}$$

$$c(x, y) = \frac{2\sigma_x\sigma_y + c_2}{\sigma_x^2 + \sigma_y^2 + c_2}; \quad \text{Formula XIV}$$

$$s(x, y) = \frac{\sigma_{xy} + c_3}{\sigma_x\sigma_y + c_3}; \quad \text{Formula XV}$$

$$SSIM = l(x, y)^\alpha \times c(x, y)^\beta \times s(x, y)^\gamma; \quad \text{Formula XVI}$$

wherein x and y respectively represent two images needing to be compared; l(x, y), c(x, y), and s(x, y) represent brightness comparison, contrast comparison, and structure comparison; $\mu_x$, $\mu_y$, $\sigma_x$, $\sigma_y$, and $\sigma_{xy}$ respectively represent a mean value of x, a mean value of y, a standard deviation of x, a standard deviation of y, and a covariance between x and y; $c_1$, $c_2$, and $c_3$ are constants, respectively, to avoid an error where the denominator is 0, $c_3=c_2/2$; and in actual calculation, $\alpha$, $\beta$, and $\gamma$ are all set to be 1.

6. The color matching evaluation method combining the similarity measure and the visual perception according to claim 1, wherein in Step 7, visual perception data is obtained by weighting according to fixed weights after normalizing three types of data: average fixation time, an average quantity of fixation points, and a first fixation duration in the eye movement tracking experiment.

7. The color matching evaluation method combining the similarity measure and the visual perception according to claim 1, wherein in Step 8, a calculation formula of the image-content-based evaluation system is as follows:

$$SIM = \omega * S + (1-\omega) * SSIM \qquad \text{Formula XVII:}$$

wherein $\omega$ is a variable weight; S is the similarity measure between the palettes, namely, the evaluation indicator I; SSIM is the structural similarity between the images, namely, the evaluation indicator II; and SIM is a final evaluation indicator.

8. The color matching evaluation method combining the similarity measure and the visual perception according to claim 1, wherein a formula of the Person correlation coefficient in Step 9 is as shown in Formula XVIII;

$$\rho = \frac{\text{cov}(XY)}{\sigma_x \sigma_y}; \qquad \text{Formula XVIII}$$

wherein X and Y are independent variables; cov(XY) represents a covariance between the variable X and the variable Y; and $\sigma$ is a standard deviation.

* * * * *